United States Patent
Zwart

(10) Patent No.: US 8,864,683 B2
(45) Date of Patent: Oct. 21, 2014

(54) BRUSH, SUCH AS FOR CLEANING OR SAMPLING BODY TISSUE

(75) Inventor: Meindert Durk Zwart, Rosmalen (NL)

(73) Assignee: MDZ Beheer B.V., Willemstad, Curacao (NL)

( * ) Notice: Subject to any disclaimer, the term of this patent is extended or adjusted under 35 U.S.C. 154(b) by 1084 days.

(21) Appl. No.: 12/096,868

(22) PCT Filed: Dec. 22, 2005

(86) PCT No.: PCT/NL2005/050092
§ 371 (c)(1),
(2), (4) Date: Aug. 14, 2008

(87) PCT Pub. No.: WO2007/073152
PCT Pub. Date: Jun. 28, 2007

(65) Prior Publication Data
US 2008/0294067 A1    Nov. 27, 2008

(51) Int. Cl.
*A61B 10/00* (2006.01)
*A46D 1/00* (2006.01)
*A61B 10/02* (2006.01)

(52) U.S. Cl.
CPC ............. *A61B 10/0291* (2013.01); *A61B 10/00* (2013.01); *A46D 1/00* (2013.01); *A61B 2010/0216* (2013.01); *A46D 1/0238* (2013.01)
USPC ........................................................ 600/569

(58) Field of Classification Search
USPC ........................................................ 600/569
See application file for complete search history.

(56) References Cited

U.S. PATENT DOCUMENTS

| 3,214,777 A | * | 11/1965 | Kutik | 15/187 |
| 5,564,151 A | | 10/1996 | Miller et al. | |
| 5,967,617 A | * | 10/1999 | Zapanta | 300/21 |
| 6,108,849 A | * | 8/2000 | Weihrauch | 15/167.1 |

(Continued)

FOREIGN PATENT DOCUMENTS

| JP | 06169816 A | * | 6/1994 | ............... A46D 1/00 |
| NL | 301 563 A | | 10/1965 | |
| WO | WO 2005060788 A1 | * | 7/2005 | ............... A46B 3/16 |

OTHER PUBLICATIONS

Martin "Is it feasible for women to perform their own Pap smears? a research question in progress", Canadian Medical Association Journal, Mar. 7, 200; 162(5).*

*Primary Examiner* — Sean Dougherty
*Assistant Examiner* — Michael C Stout
(74) *Attorney, Agent, or Firm* — John S. Sopko; Hoffmann & Baron, LLP

(57) ABSTRACT

The present invention relates to a brush (1) for cleaning or sampling body tissue. The brush (1) comprises a support (2) that is provided with at least one row (3) of brush hairs (5) as well as one second row (4) of brush hairs (16). The first and second rows are mutually parallel and are situated next to one another. Each brush hair (5,6) has a proximal end (7) facing the support (2) and a distal end (9) facing away from the support (2). The first row (3) of brush hairs (5) comprises a strip (30) that extends in the longitudinal direction of the first row (3) and a longitudinal side (32) of which is fixed to the support (2). The proximal ends (7) of the brush hairs (5) in the first row (3) are fixed to the other longitudinal side (34) of the strip (30).

31 Claims, 3 Drawing Sheets

(56) References Cited

U.S. PATENT DOCUMENTS

| | | |
|---|---|---|
| 6,193,674 B1 | 2/2001 | Zwart |
| D561,333 S * | 2/2008 | Zwart .......................... D24/119 |
| 2005/0009063 A1* | 1/2005 | Xia et al. ......................... 435/6 |
| 2005/0022323 A1* | 2/2005 | Chan .............................. 15/22.1 |

* cited by examiner

BRUSH, SUCH AS FOR CLEANING OR SAMPLING BODY TISSUE

CROSS-REFERENCE TO RELATED APPLICATION:

This application is the National Stage of International Application No. PCT/NL2005/050092, filed Dec. 22, 2005, the contents of which is incorporated by reference herein.

FIELD OF THE INVENTION

The present invention relates to a brush, such as in particular for cleaning or sampling body tissue, where the brush comprises a support which is provided with at least one first row of brush hairs as well as at least one second row of brush hairs;
wherein said first and second row of brush hairs are situated next to one another;
wherein each brush hair has a proximal end facing the support and a distal end facing away from the support; and
wherein the distal ends of the brush hairs in said first row and said second row, viewed in a direction transverse to said rows, are located in each case at about the same distance from the support.

BACKGROUND OF THE INTVENTION

A brush is disclosed in NL 1 010 709. This brush is suitable for making a smear. This known brush has mutually parallel and essentially identical rows of brush hairs. A sample to be taken can be picked up in between the brush hairs. The brush hairs are all equally long. The brush hairs in this known brush all have a proximal end facing the support that is located directly on the support itself.

SUMMARY OF THE INVENTION

The aim of the present invention is to provide a brush, such as in particular for cleaning or sampling body tissue, which brush can free up material, such as tissue, better in order subsequently to retain this in the brush so that it can be removed for sampling or cleaning an underlying structure, such as tissue. This aim is in contrast to the state of the art in general as well as in contrast to the publication NL 1 010 709 discussed above.

The abovementioned aim is achieved according to the invention by providing a brush, such as in particular for cleaning or sampling body tissue, where the brush comprises a support which is provided with at least one first row of brush hairs as well as at least one second row of brush hairs;
wherein said first and second row of brush hairs are situated next to one another so as to be able to pick up tissue material between them;
wherein each brush hair has a proximal end facing the support and a distal end facing away from the support;
wherein the first row of brush hairs comprises a strip that extends in the longitudinal direction of the first row and a longitudinal side of which is fixed to the support; and
wherein the proximal ends of the brush hairs in said first row are fixed to the other longitudinal side of the strip.

By providing the brush hairs of the so-called first row of brush hairs on a strip, on the one hand the scraping action of the brush hairs fixed to said strip is improved because the strip effectively makes the hairs stiffer, as a result of which the material, such as tissue material, is freed up better and, on the other hand, what is achieved is that the capacity for retaining material, such as tissue, in the brush is not significantly different to that in the case of a brush with brush hairs that are not arranged on a strip and have a length equal to the height of the strip plus the length of the brush hairs fixed thereon. The material scraped free that is to be removed for sampling or cleaning is retained between the brush hairs and/or between brush hairs and one or more strips and/or between adjacent strips.

According to the invention tissue is understood to be material obtained from a human or animal body in the widest sense. This material can be inter alia cell material originating from the skin or from body cavities or otherwise from the inside of the body, mucus, fluid as well as debris from wounds, such as pus.

According to a more detailed embodiment the distal ends of the brush hairs in said first row and in said second row are located in each case at about the same distance from the support. In this way, when material is collected, optimum interaction between the first and second row is obtained. Here, 'at about the same distance' is thus at least understood to be a difference in distance of 10-30% or 1-3 mm. If the first row is too much shorter than the second row, then the effect of the stiffening action of the strip for the first row will rapidly start to diminish. If the first row is too much longer than the second row, freed up material will no longer be collected properly in the brush.

According to a more detailed embodiment the first and second row of brush hairs are mutually parallel. In this way the ability to collect tissue material in between said rows is the same along the entire portion where these rows of brush hairs are situated next to one another.

According to the invention, viewed in the transverse direction of said row, the thickness of the strip will be equal to 50% to 200% of the thickness of the proximal ends of the brush hairs fixed to said strip. For example, if the brush hairs fixed to said strip have a thickness of approximately 0.25 mm, then the thickness of the strip will lie in the range of 0.125 mm to 0.5 mm.

According to a further advantageous embodiment of the invention the at least one second row of brush hairs is essentially the same as the at least one first row of brush hairs and/or yet another first row of brush hairs is situated directly next to a first row of brush hairs. The invention thus very clearly makes provision that in a brush all rows of brush hairs can be made as a so-called first row of brush hairs, i.e. as a strip with the brush hairs mounted thereon. However, the present invention very clearly makes provision that a first row of brush hairs (with strip) can be provided between ordinary brush hairs (without strip).

In particular the invention also makes provision that the brush has 2, 3 or more said first rows of brush hairs, which are mutually parallel and are situated alongside one another.

It is advantageous according to a further embodiment of the invention if said first row of brush hairs is composed of two bands of mutually offset hair members, the two bands being situated alongside and in contact with one another;
if each hair member has a distal and a proximal portion;
if the proximal portion of each hair member from the one band of hair members overlaps the proximal portion of the adjacent hair members from the other band of hair members in an overlap zone in each case and, in the overlap zones, said hair members are joined as a unit such that the proximal portions of said hair members of the mutually offset hair member bands situated alongside and in contact with one another form the said strip. With this arrangement in particular the distal portions of said hair members will then form the brush hairs of said first row of brush hairs.

Joining the hair members in the overlap zones as a unit can as such be effected in a wide variety of ways. This can be by gluing together, although this can also be achieved very simply by forming said first row of brush hairs by injection moulding plastic in such a way that the hair members together form a unit in the overlap zones.

With this arrangement, it is advantageous according to a further embodiment of the invention if each hair member has a cross-section in the form of a triangle with a base side and if said base sides of the mutually offset hair member bands situated alongside one another are mutually parallel and face one another. What is achieved in this way is that the strip, viewed in the longitudinal direction, has a wavy path. This wavy path improves the ability of the brush to retain material to be removed for sampling or cleaning in the brush. The shape of the triangle can in this case be the shape of an isosceles triangle, the base side of which then extends between the ends of the equal arms pointing away from one another (here an isosceles triangle is understood to be a triangle with two equal sides). The sides of the triangular shape provide, in each band, reinforcement for improved scraping action when scraping in the direction in which the base surface faces. Because the base surfaces of the one band face in the opposite direction with respect to the base surfaces from the other band, what is achieved is that the brush is not directionally dependent, at any rate can scrape in two opposing directions. With a brush that can be rotated for scraping, the brush can then be rotated in both directions. This appreciably increases the ease of use of the brush.

In order to improve the scraping action of the brush according to the invention further, it is advantageous according to the invention if the brush hairs taper in the distal direction and are truncated at the distal ends. This thus achieves that said brush hairs determine a linear scraping surface at the distal end instead of (without truncation) having a pointed end. A pointed end is relatively much softer, as a consequence of the thinness, as a result of which the scraping action would be less good. Truncation provides more stiffness at the distal ends.

In order to improve the ability to retain material in the brush it is advantageous according to the invention if the strip, viewed in the longitudinal direction of said strip, has a wavy path.

It is furthermore advantageous according to the invention if the support and said at least one first row of brush hairs is made as a one-piece injection moulded product, in particular made of plastic. In this way the brushes can be manufactured in large numbers at acceptable costs.

According to a further embodiment of the invention the support is an elongated member that on at least two opposing sectors of the longitudinal wall thereof is provided with at least one said first row of brush hairs. In this way a brush is obtained with a scraping zone on two opposing longitudinal sides.

According to a further embodiment of the invention the support comprises an elongated member that is provided with a plurality of these said first rows of brush hairs all round. In this way a brush is obtained with an improved scraping action all round.

With the abovementioned embodiments with elongated support, it is furthermore advantageous if said first rows of brush hairs extend in the longitudinal direction of said elongated member. In this way a scraping effect can be achieved by rotation of the elongated organ around its longitudinal axis.

According to a further embodiment of the brush with elongated support, the thickness of the brush, viewed transversely to the longitudinal direction of the support, is less than about 20 mm, in particular less than 15 mm, such as about 10 mm or less.

According to a further embodiment of the invention the brush has a handle attachment with which the support can be fitted on a handle and the support is provided with at least one said first row of brush hairs that ran in the axial direction of the handle.

According to a more detailed embodiment of a brush according to the invention the centre-o-centre distance between a said first row of brush hairs and an adjacent row of brush hairs is less than about 3 mm, such as less than 1.5 mm, in particular is less than approximately 1 mm.

According to a further, more detailed embodiment of the invention the brush hairs have a cross-sectional surface area less than about 1 $mm^2$, such as less than about 0.3 $mm^2$, in particular less than 0.1 $mm^2$. The brush hairs can, for example, have at their proximal end—where they are generally thickest, a cross-sectional surface area of about 0.06 $mm^2$.

According to a further aspect the invention relates to the use of a brush according to the invention for cleaning or sampling body tissue.

In particular the invention relates to the use of a brush according to the invention for taking a sample for cytological examination of fluid.

Furthermore, the brush according to the invention can be used very readily for taking samples from the mouth or pharynx as well as for taking a cervical smear.

In the general sense the brush according to the invention can be used for cleaning and/or sampling body cavities, where the material collected can be used for cytological/pathological examination (cell material, biopsy), bacteriological examination (for example on pus), viral examination and/or DNA examination.

BRIEF DESCRIPTION OF THE DRAWING

In the following the invention will be explained in more detail with reference to the appended drawing. In this drawing:

FIG. 2A showing a side view and 2B showing a sectional view according to arrows II-II in FIG. 2A;

DETAILED DESCRIPTION OF PREFERRED EMBODIMENT

Figure 1:
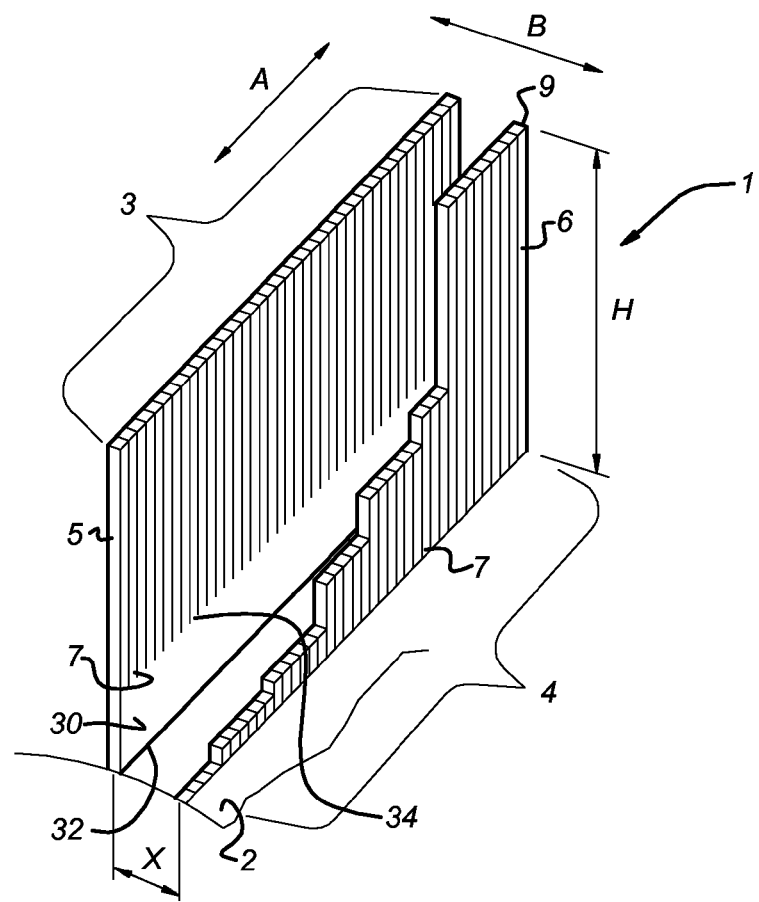
FIG. 1 shows very diagrammatically and in perspective a brush according to a first embodiment of the invention.

FIG. 1 shows a first embodiment of a brush 1 according to the invention. This brush 1 comprises a support 2, of which only a portion is drawn. Two rows 3, 4 of brush hairs are provided on this support 2. The row 3 is a so-called first row of brush hairs 5 and the row 4 is a so-called second row of brush hairs 6. The brush hairs 5 and 6 each have a distal end 9 facing away from the support 2 and a proximal end 7 facing the support 2. In the second row 4 the brush hairs 6—as is usual and known from the state of the art—are fixed at the proximal ends 7 to the support.

In the first row 3 the proximal ends 7 of the brush hairs 5 are not directly fixed to the support 2 themselves. At this location a strip 30 is provided between the proximal ends 7 and the support 2. This strip 30 extends in the longitudinal direction of the first row 3 and is fixed to the support 2 at a longitudinal side 32. The proximal ends 7 of the brush hairs 5 are fixed to the other longitudinal side 34 of the strip 30.

The strip 30 gives the hairs 5 of the first row extra sturdiness. Because the strip 30 in itself constitutes a stiffer construction in its height direction than the brush hairs 5 in their longitudinal direction, the strip gives the hairs 5, as it were, extra stiffness—while the distance from the distal ends 7 to the support 2 can remain essentially the same. This extra stiffness helps the scraping action of the brush. The collection capacity of the brush (that is to say, the capacity to collect material between the brush hairs) is principally determined by the space between the brush hairs. The distance H from the distal ends of the brush hairs to the support is an important factor in this. Because this can remain essentially the same the collection capacity of the brush is left intact, whilst the scraping ability is improved by stiffening at least a part of the brush hairs.

The brush hairs 6 in the second row 4 all have a length H here. The hairs 5 of the first row all have a length less than H here. In the second row, the height of the strip 30 plus the length of the brush hairs 5 together is equal to H. Thus the distal ends 7 of the brush hairs 5 and 6 in both rows 3 and 4 are at a distance H above the surface of the support 2. It is pointed out that, viewed in the longitudinal direction A of the rows, the lengths of the brush hairs can very likely vary. However, viewed in a direction transverse to said rows, the distal ends of neighbouring brush hairs from the first 3 and second 4 row will be located in each case at about the same distance H from the support. It is pointed out that by 'in each case at about the same distance' the invention also means cases where said 'distance H from the support to the distal hair end 9' between neighbouring hairs 5, 6 in both rows differs by 30%. Therefore if the distal ends 9 of the hairs 5 are located at approximately 1 cm from the support 2, then according to the invention the distal ends 9 of the hairs 6 can very likely be 15% closer or further away and thus be located at 0.85 or 1.15 cm from the support 2. What is concerned here is that the neighbouring brush hairs in one and the same row and in adjacent rows mutually work together when scraping and collecting tissue material.

FIG. 1 shows a single first row 3 and a single second row 4. It will be clear that many variants are conceivable. For instance, within the scope of the claims it is certainly conceivable that:
- the second row 4 is made identical to the first row 3—thus with strip 30; or
- on the other side of the first row 3 another second row 4 or even another first row 3 is provided; or
- the brush has a plurality of rows of brush hairs with in each case per, for example, 1, 2, 3, 4 or 5 ordinary, so-called second rows, one so-called first row to improve the scraping ability.

In the embodiment according to FIG. 1 the strip 30 is a flat, rectilinear strip in the longitudinal direction A. If the row follows a curved path, the strip 30 will follow a correspondingly curved path and will still be flat, essentially rectilinear. However, it is according to the invention highly advantageous if the strip, viewed in the longitudinal direction (A) of the row of brush hairs, has a wavy path. The strip then, as it were, meanders about a main direction of extension. The wavy shape improves the ability of the brush to keep collected material retained in the brush. Such a wavy shape can be implemented easily by making a flat strip of material wave-shaped. Another mode of implementation is shown with reference to FIGS. 2A and 2B. Moreover, such a wavy shape contributes to further improvement in the scraping action because the brush hairs are thereby effectively further stiffened. A wavy strip is stiffer in the transverse direction thereof than a completely flat strip.

Figure 2A:
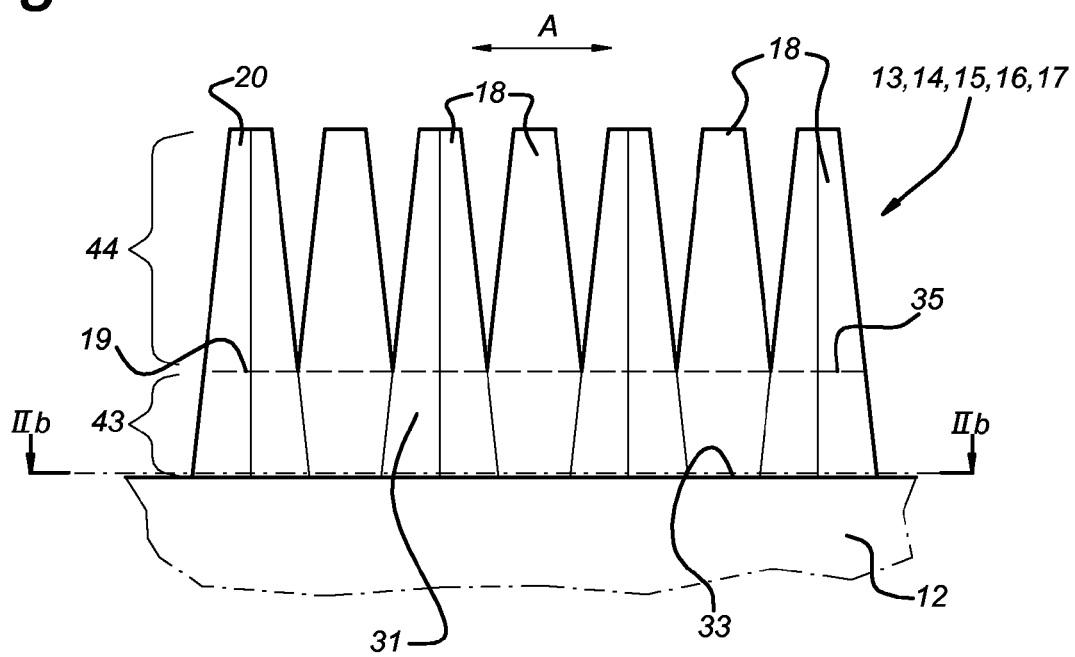
FIGS. 2A and 2B show very diagrammatically the composition of a portion of a so-called first row of brush hairs of the brush according to FIGS. 3 and 4.
Figure 2B:
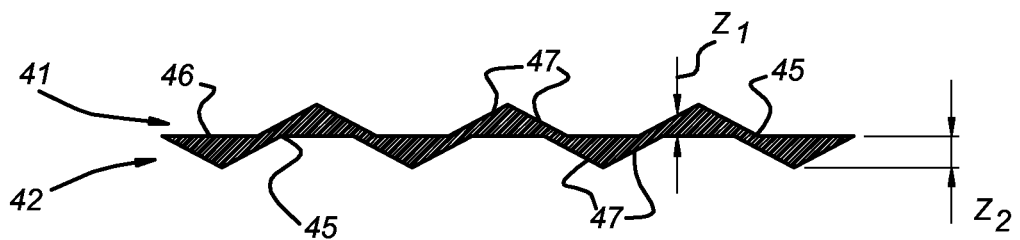
Figure 3:
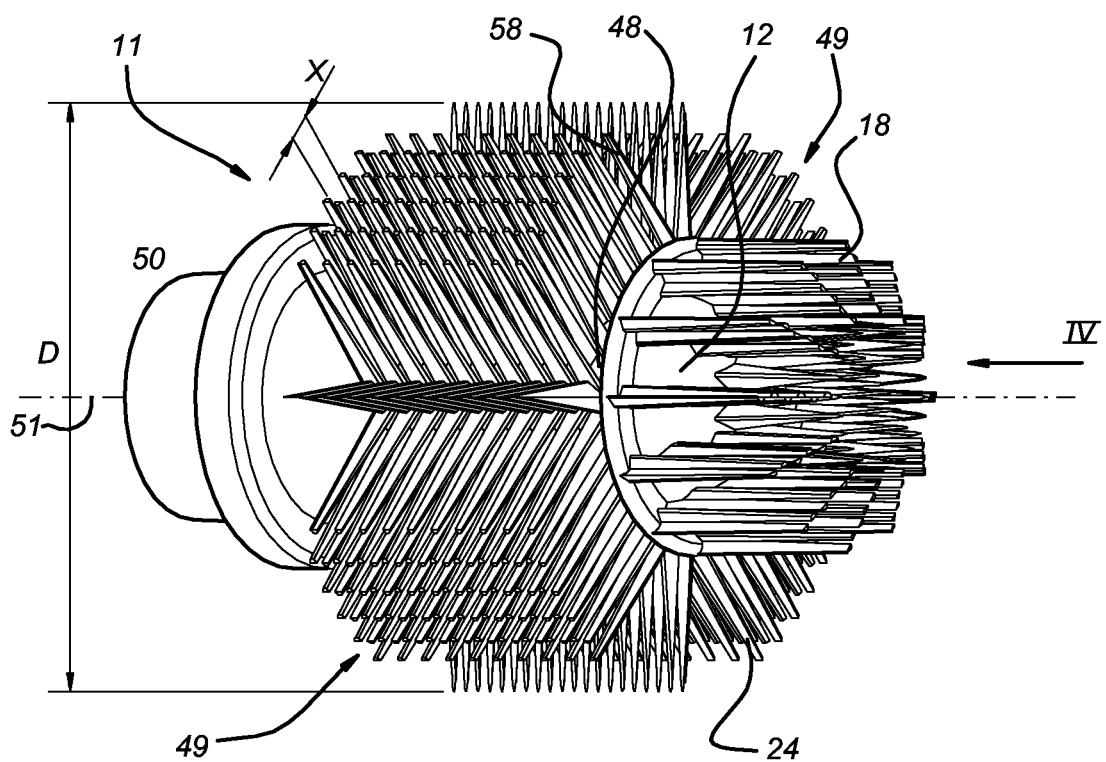
FIG. 3 shows a perspective view of a brush according to a second embodiment of the invention.
Figure 4:
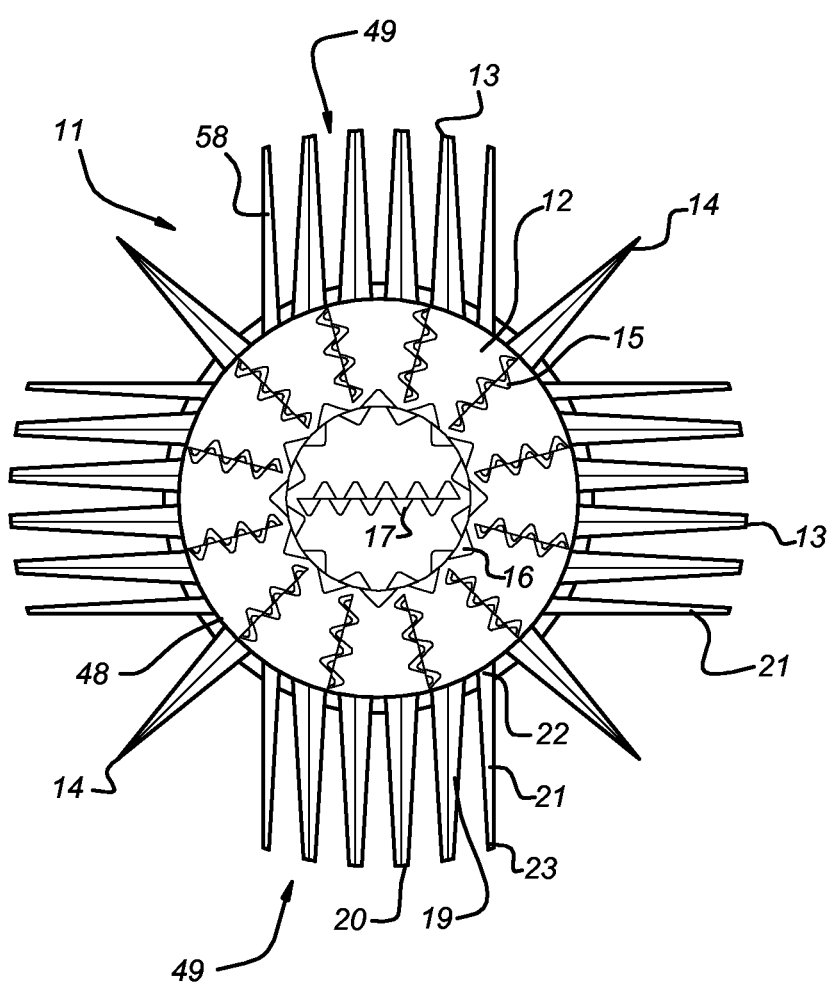
FIG. 4 shows a front end view according to arrow IV in FIG. 3 of the brush shown therein.

FIGS. 2A and 2B show schematically in side view and section, respectively, how the rows 13, 14, 15, 16 and 17 of the brush shown in FIGS. 3 and 4 are composed.

As can be seen in particular in FIG. 2B, the row 13, 14, 15, 16, 17 is composed of two bands of hair members, the two bands being located alongside and in contact with one another. In this example the hair members have a triangular cross-section. Two hair members from the upper band 41 in FIG. 2B are shown and three hair members from the lower band 42 in FIG. 2B are shown. Furthermore, it can be seen in the FIGS. 2A and 2B that the hair members from the one band 41 are arranged offset with respect to the hair members from the other band 42. The hair members from the one band 41 and the other band 42 overlap one another in overlap zones 45. At this point the hair members from the one band and the hair members from the other band are mutually joined—fixed to one another—so as in this way to form a strip 31 comparable to the strip 30 in FIG. 1. As a result of the triangular cross-sectional shape of the hair members, this strip 30 has a wavy path. As explained above this wavy path has advantages with regard to the ability of the brush to keep collected tissue retained as well as with regard to improving the scraping action by additional stiffening.

The strip 30 has a lower longitudinal side 33, see FIG. 2A, with which the hair members/the strip 30 is fixed to the support 12 and an upper longitudinal side 35 from where the hair members stand up separately from one another. The brush hairs 18 in the rows 13, 14, 15, 16, 17 are thus formed by the distal portion 44 of the hair members. The proximal portions 43 of the hair members together form the strip 33. The proximal ends 19 of the brush hairs 18 are fixed to the strip 31. Because the hair members are essentially in one piece this fixing will essentially be a transition rather than a joint.

With reference to FIG. 2B each hair member has a triangular cross-section and the triangular shapes are in the form of isosceles triangles. In this case two equal arms 47 and a base 46 are concerned per hair member.

With reference to FIG. 2A it can be seen that the hair members taper in the distal direction and have a truncated distal end 20. This truncated distal end 20 improves the scraping action of the brush hairs 18. Were the hairs to taper completely to a peak, then the hairs would be very soft at the distal end.

In FIG. 2B the thickness of the strip is, moreover, indicated by Z. This thickness here is approximately equal to the thickness of the proximal ends 19 of the brush hairs 18. As a result of the tapering of the hair members 43, 44 in the distal direction the thickness Z will on balance be somewhat greater than the thickness of the proximal ends of the brush hairs. If a choice is made to make a flat strip instead of a wavy strip 31 and nevertheless to retain the two bands 41 and 42 of brush hairs, then the thickness of the strip would be approximately equal to twice the thickness of the proximal end 19 of the hair members.

FIGS. 3 and 4 show a brush provided with rows 13, 14, 15, 16 and 17 of brush hairs, made up as described above with reference to FIGS. 2A and 2B.

The brush in FIGS. 3 and 4 is indicated in its entirety by 11. The brush has a handle attachment 50 for fixing on a handle.

The handle can be inserted in this handle attachment 50 or the handle attachment 50 can be inserted in a hollow end of the handle.

An elongated support 12 extends from the handle attachment 50. This support has, as it were, four 90° sectors situated separately around the longitudinal axis 50. Two of the opposing sectors are indicated by 49. Each of these sectors has four rows 13 and each sector is flanked on both sides by a row 58. The rows 58 consist essentially of a single band 41 or 42 (see FIGS. 2A and 2B). A row 14 is provided in each case in the middle in between the sectors. Both the rows 13 and 14 are made up in accordance with FIGS. 2A and 2B. The rows 13, 14 and 58 all extend parallel to the longitudinal axis 51 of the support/handle. The brush hairs are oriented radially or roughly radially with respect to the support.

At the front end of the support radial rows 15 are provided, one circular row 16 and one straight central row 17. The hairs in all these rows are oriented essentially axially with respect to the support/handle. The radial rows 15 run essentially mutually parallel. The rows 15, 16 and 17 are all made up in accordance with FIGS. 2A and 2B.

It is pointed out that for the brush as shown in FIGS. 3 and 4 many variants that fall within the scope of the invention determined by the claims are conceivable, such as inter alia:

- The rows 15, 16 and 17 of axial hairs can be completely omitted, whilst the rows 13 and/or 14 and/or of radial hairs are ordinarily present; or
- The rows 13, 14 and 58 of radial hairs can be completely omitted, whilst the rows 15, 16 and 17 of axial hairs are present; and/or
- The number of rows 13 and/or 15 and/or 14 can vary; and/or
- The rows 58 and/or 16 and/or 17 can be omitted; and/or
- The rows 15 can be replaced by concentric circular rows 16; etc.

The brush according to the invention is suitable for a variety of applications. These applications can also fall outside the area of 'cleaning or sampling body tissue'. The following can inter alia be mentioned as applications in the field of cleaning or sampling body tissue:

- Oral sampling: In this case the correct stiffness of the brush hairs is important because deeper lying cells also have to be collected/sampled. The geometry is also of importance. Sometimes only the sides of the brush will be used and sometimes particularly the front will be used (for example for certain parts of the cheek).
- Cervical, vaginal, anal or intestine sampling: The brush according to the invention can essentially be used for all body cavities. The sizes and shape of the brush can vary per application area, so the sizes and shape, respectively, are adapted to the body cavity concerned.
- Cytological, pathological (cell material, biopsy) examination, bacteriological examination, viral examination, DNA examination.

With regard to the use of the brush according to the invention for medical investigation it is pointed out that the taking of the sample is not an activity that is reserved for medical personnel. The patient can usually take the sample him/herself, such as is known inter alia for cervical smears, anal smears, DNA smears, etc.

What is claimed is:

1. A brush for sampling body tissue,
   where the brush comprises a support which is provided with at least one first row of brush hairs as well as at least one second row of brush hairs;
   wherein said first and second row of brush hairs are situated next to one another;
   wherein each brush hair has a proximal end facing the support and a distal end facing away from the support;
   wherein the first row of brush hairs comprises a strip that extends in the longitudinal direction of the first row and a longitudinal side of which is fixed to the support;
   wherein the proximal ends of the brush hairs in said first row are fixed to the other longitudinal side of the strip;
   wherein each brush hair of the first row has a length less than the distance from the distal end of said each brush hair of the first row to the support;
   wherein said first row of brush hairs is composed of two bands of longitudinally offset hair members, the two bands being situated alongside and in contact with one another;
   wherein each hair member has a distal and a proximal portion;
   wherein the proximal portion of each hair member from the one band of hair members overlaps a portion of the proximal portion of the adjacent ones of said offset hair members from the other band of hair members in an overlap zone in each case and, in the overlap zones, said hair members are joined as a unit such that the proximal portions of said hair members of the longitudinally offset hair member bands situated alongside and in contact with one another form the strip; and
   wherein the support comprises an elongated member that on at least two opposing sectors of a longitudinal wall thereof is provided with at least one said first row of brush hairs.

2. A brush for sampling body tissue,
   where the brush comprises a support which is provided with at least one first row of brush hairs as well as at least one second row of brush hairs;
   wherein said first and second row of brush hairs are situated next to one another;
   wherein each brush hair has a proximal end facing the support and a distal end facing away from the support;
   wherein the first row of brush hairs comprises a strip extending in the longitudinal direction of the first row, the strip having opposed first and second longitudinal sides, said first opposed longitudinal side being fixed onto the support, and onto said second opposed longitudinal side are fixed the proximal ends of the brush hairs in said first row such that the strip is provided between the support and the proximal ends of the brush hairs in said first row to define a spacing between the support and the proximal ends of the brush hairs in said first row;
   wherein said first row of brush hairs is composed of two bands of longitudinally offset hair members, the two bands being situated alongside and in contact with one another;
   wherein each hair member has a distal and a proximal portion;
   wherein the proximal portion of each hair member from the one band of hair members overlaps a portion of the proximal portion of the adjacent ones of said offset hair members from the other band of hair members in an overlap zone in each case and, in the overlap zones, said hair members are joined as a unit such that the proximal portions of said hair members of the longitudinally offset hair member bands situated alongside and in contact with one another form the strip; and
   wherein the support comprises an elongated member that on at least two opposing sectors of a longitudinal wall thereof is provided with at least one said first row of brush hairs.

3. The brush according to claim 2, wherein the distal ends of the brush hairs in said first row and said second row, viewed in a direction transverse to said rows, are located in each case at about the same distance (H) from the support.

4. The brush according to claim 2, wherein the first and second rows of brush hairs are mutually parallel.

5. The brush according to claim 2, wherein the at least one second row of brush hairs is essentially the same as the at least one first row of brush hairs.

6. The brush according to claim 2, having 2, 3 or more said first rows of brush hairs, which are mutually parallel and are situated alongside one another.

7. The brush according to claim 2, wherein the distal portions of said hair members form the brush hairs of said first row of brush hairs.

8. The brush according to claim 2, wherein each hair member has a cross-section in the form of a triangle with a base side and wherein the base sides of the longitudinally offset hair member bands situated alongside and in contact with one another are mutually parallel and face one another.

9. The brush according to claim 8, wherein the triangle is an isosceles triangle, the base side of which extends between the ends of the equal arms pointing away from one another.

10. The brush according to claim 2, wherein brush hairs taper in the distal direction and are truncated at the distal ends.

11. The brush according to claim 2, wherein the strip, viewed in the longitudinal direction of said row, has a wavy path extending in a plane transverse to a length direction of the hairs.

12. The brush according to claim 2, wherein the support and said at least one first row of brush hairs is made as a one-piece injection moulded product of plastic.

13. The brush according to claim 2, wherein the support comprises an elongated member that is provided with a plurality of these said first rows of brush hairs all round.

14. The brush according to claim 1, wherein said first rows of brush hairs extend in the longitudinal direction of said elongated member.

15. The brush according to claim 1, wherein, viewed transversely to the longitudinal direction of the support, the thickness (D) of the brush is less than about 20 mm.

16. The brush according to claim 2, having a handle attachment with which the support can be fitted on a handle, wherein the support is provided with at least one said first row of brush hairs that run in the longitudinal direction of the handle.

17. The brush according to claim 2, wherein the centre-to-centre distance (X) between a said first row of brush hairs and an adjacent row of brush hairs is less than about 3 mm.

18. The brush according to claim 2, wherein the cross-section of the brush hairs is less than about 1 $mm^2$.

19. The brush according to claim 2, wherein the thickness (Z1, Z2) of the strip is equal to 50% to 200% of the thickness of the proximal ends of the brush hairs fixed to the strip.

20. A method of using a brush according to claim 2 for sampling body tissue, wherein tissue material is scraped free from the body tissue by the brush hairs and retained between the brush hairs and/or between adjacent strips.

21. A method of using a brush according to claim 2 for taking a sample for cytological examination of fluid and/or for bacteriological examination and/or for viral examination and/or for DNA examination, wherein tissue material is scraped free by the brush hairs and retained between the brush hairs and/or between adjacent strips.

22. A method of using a brush according to claim 2 for taking a sample from the mouth or pharynx, wherein tissue material is scraped free by the brush hairs and retained between the brush hairs and/or between adjacent strips.

23. A method of using a brush according to claim 2 for taking a cervical smear, wherein tissue material is scraped free by the brush hairs and retained between the brush hairs and/or between adjacent strips.

24. The brush according to claim 2, wherein the centre-to-centre distance (X) between a said first row of brush hairs and an adjacent row of brush hairs is less than 1.5 mm.

25. The brush according to claim 2, wherein the centre-to-centre distance (X) between a said first row of brush hairs and an adjacent row of brush hairs is less than about 1 mm.

26. The brush according to claim 2, wherein the cross-section of the brush hairs is less than about 0.3 $mm^2$.

27. The brush according to claim 2, wherein the cross-section of the brush hairs is less than 0.1 $mm^2$.

28. The brush according to claim 1, wherein, viewed transversely to the longitudinal direction of the support, the thickness (D) of the brush is less than about 10 mm.

29. The brush according to claim 1, wherein the proximal ends of the brush hairs in said second row are fixed directly to said support.

30. The brush according to claim 1, wherein the support comprises an elongated member that on at least two pairs of two opposing sectors of the longitudinal wall of the elongate member are each provided with at least one said first row of brush hairs.

31. The brush according to claim 2, wherein the support comprises an elongated member that on at least two pairs of two opposing sectors of the longitudinal wall of the elongate member are each provided with at least one said first row of brush hairs.

* * * * *